US010307537B2

(12) United States Patent
Wei

(10) Patent No.: US 10,307,537 B2
(45) Date of Patent: Jun. 4, 2019

(54) LIQUID PARAMETER DETECTING METHOD AND SYSTEM

(71) Applicant: BOE TECHNOLOGY GROUP CO., LTD., Beijing (CN)

(72) Inventor: Chuang Wei, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 166 days.

(21) Appl. No.: 15/503,800

(22) PCT Filed: Aug. 3, 2016

(86) PCT No.: PCT/CN2016/093067
§ 371 (c)(1),
(2) Date: Feb. 14, 2017

(87) PCT Pub. No.: WO2017/117998
PCT Pub. Date: Jul. 13, 2017

(65) Prior Publication Data
US 2018/0207362 A1 Jul. 26, 2018

(30) Foreign Application Priority Data
Jan. 4, 2016 (CN) .......................... 2016 1 0003602

(51) Int. Cl.
A61M 5/14 (2006.01)
G01N 9/04 (2006.01)
G01N 9/24 (2006.01)
A61M 5/172 (2006.01)
A61M 5/168 (2006.01)
G01F 23/20 (2006.01)
G01N 9/36 (2006.01)

(52) U.S. Cl.
CPC .......... *A61M 5/172* (2013.01); *A61M 5/1417* (2013.01); *A61M 5/16886* (2013.01);
(Continued)

(58) Field of Classification Search
CPC ............ A61M 5/1417; A61M 5/16886; A61M 5/16895; G01F 23/20; G01N 9/04; G01N 9/36
(Continued)

(56) References Cited

U.S. PATENT DOCUMENTS 4,280,126 A * 7/1981 White ................. G01F 23/2965
340/621
2008/0027409 A1 1/2008 Rudko et al.
(Continued)

FOREIGN PATENT DOCUMENTS

CN 102028990 A 4/2011
CN 103330984 A 10/2013
(Continued)

OTHER PUBLICATIONS

English translation of PCT International Search Report, Application No. PCT/CN2016/093067, dated Oct. 28, 2016, 2 pages.
(Continued)

Primary Examiner — Jonathan M Dunlap
(74) Attorney, Agent, or Firm — Armstrong Teasdale LLP

(57) ABSTRACT

A liquid detection system for detecting a liquid level position of a liquid in a hanging bottle includes a hanging bottle casing unit for determining the overall gravity of the hanging bottle, a hanging bottle cap unit for determining the liquid density in the hanging bottle, and a transmission unit for transmitting the overall gravity and liquid density of the hanging bottle to a server, and the server. The server is configured to determine the liquid gravity in the hanging bottle, calculate the liquid volume in the hanging bottle based on the liquid gravity and the liquid density, and determine a liquid level position based on the liquid volume.

18 Claims, 7 Drawing Sheets

(52) U.S. Cl.
CPC ............... *G01F 23/20* (2013.01); *G01N 9/04* (2013.01); *G01N 9/24* (2013.01); *G01N 9/36* (2013.01); *A61M 5/1684* (2013.01); *A61M 2205/18* (2013.01); *A61M 2205/3375* (2013.01); *A61M 2205/3393* (2013.01); *A61M 2205/3584* (2013.01)

(58) Field of Classification Search
USPC .......................................................... 73/296
See application file for complete search history.

(56) References Cited

U.S. PATENT DOCUMENTS

2011/0205074 A1* 8/2011 Feng et al. .......... A61M 5/1414
340/613

2015/0346013 A1* 12/2015 Feng et al. .......... A61M 5/1414
702/55

FOREIGN PATENT DOCUMENTS

| CN | 103656792 A | 3/2014 |
|----|-------------|--------|
| CN | 104122170 A | 10/2014 |
| CN | 204049662 U | 12/2014 |
| CN | 105194759 A | 12/2015 |
| CN | 105435337 A | 3/2016 |
| DE | 19955368 A1 | 5/2001 |

OTHER PUBLICATIONS

PCT Written Opinion, Application No. PCT/CN2016/093067, dated Oct. 28, 2016, 10 pages.: with English translation of relevant part.
China First Office Action, Application No. 201610003602.1, dated Aug. 5, 2016, 18 pps.: with English translation.

* cited by examiner

Measurement ranges and structural dimensions
| Dimensions (mm) Ranges (Kg) | ΦA | ΦC | ΦD | H | E |
|---|---|---|---|---|---|
| 20 - 200kg | 20 | 2.5 | 15.5 | 12 | 10 |
| 500kg - 1t | 28 | 5.4 | 17 | 15 | 11.5 |
Structural dimensions: (unit: mm)
Fig. 5
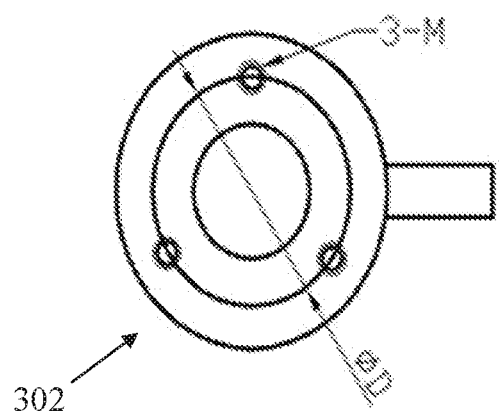
Fig. 5A
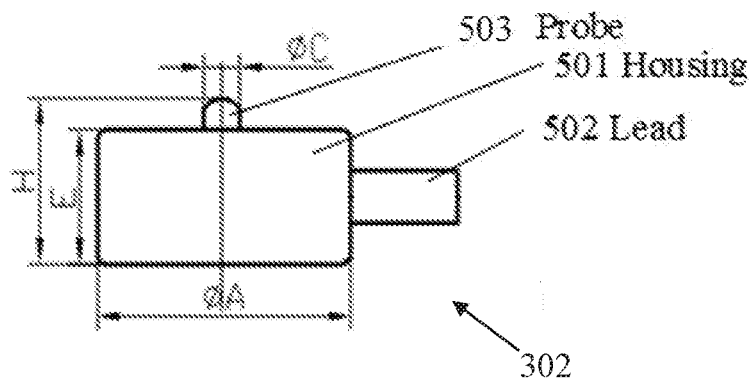
Fig. 5B

LIQUID PARAMETER DETECTING METHOD AND SYSTEM

CROSS REFERENCE TO RELATED APPLICATIONS

This application is a National Stage Entry of PCT/CN2016/093067 filed Aug. 3, 2016, which claims the benefit and priority of Chinese Patent Application No. 201610003602.1 filed Jan. 4, 2016, the entire disclosures of which are incorporated herein by reference.

BACKGROUND

The present disclosure relates to the field of medical devices, and more particularly to a liquid parameter detection method and system.

At present, in the field of medical equipment, hanging bottles are used widely. Typically, a hanging bottle consists of a hanging bottle body and a hanging bottle cap. In the case of a hanging bottle used for infusion, an infusion needle is first inserted through the hanging bottle cap into the liquid. The hanging bottle is then hung high and upside down, so that the liquid passes from the hanging bottle through the infusion tube directly into the patient by means of the gravitational potential. However, when the liquid (for example, a medical liquid) in the hanging bottle is about to run out, if there is no accompanying staff to promptly unplug the infusion tube, it is easy to cause a blood backstreaming phenomenon. The blood backstreaming phenomenon may lead to a medical accident, and when serious, may be life-threatening to the patient.

With the rapid development of medical device technology, various types of medical sensors, as well as supporting technology applicable to medical devices, emerge. There is a need in the art for a device that can determine in real time parameters such as liquid density, liquid gravity, and liquid level inclination in a hanging bottle. The device must also be capable of transmitting and displaying various parameters to healthcare personnel, patients and family members of patients in a timely manner. By judging the parameters of liquid density, liquid gravity, and liquid level inclination, the liquid level can be determined and appropriate signals, such as warnings on liquid level, flow rate, or tilt can be issued when necessary to prevent the occurrence of medical accidents caused by problems of the hanging bottle, such as blood backstreaming occurring in the absence of a caregiver beside the patient, and other problems.

When determining the liquid volume and the liquid level, it may be necessary to determine the liquid density in the hanging bottle. In using a hanging bottle for drip infusion, usually other liquids are injected into the original liquid of the hanging bottle. For example, penicillin is injected into a 50% glucose bottle. The mixing of the medical liquids may cause a change in the liquid density in the hanging bottle, and the liquid density in the hanging bottle varies according to the type and amount of the medical liquids injected. Therefore, in order to be able to accurately measure the parameters associated with the liquid in the hanging bottle, the liquid density in the hanging bottle must be accurately determined.

The design of an existing liquid parameter detection system in a hanging bottle is complex, and it is necessary to modify the whole bottle to achieve the purpose of detecting the liquid parameters. Existing detection systems are costly, difficult to recycle, low in reusability, and not easy to disassemble.

On the other hand, when the existing liquid level detecting system detects the level of the liquid in the hanging bottle, it is necessary for the detecting member to contact with the liquid, so that the liquid is inevitably contaminated.

Accordingly, there is a need in the art for improved methods and systems for the detection of liquid parameters.

BRIEF DESCRIPTION

In order to reduce costs and facilitate ease of use and re-use, there is a need for a liquid parameter detection system to be integrated into a hanging bottle casing and hanging bottle cap, so that the hanging bottle does not need to be transformed. In addition, the liquid parameters need to be determined in a non-contact way in real time by weight and density measurements to avoid contamination of the liquid.

To this end, the disclosure may integrate the wireless transmission module in the detection system, transmit the liquid parameters through the Internet, and display and set related parameters on an application program of a terminal device. Users can interact well with the hanging bottle system, thus achieving a user-friendly design.

According to an aspect of the present disclosure, there is provided a liquid detection system for detecting a liquid level position of a liquid in a hanging bottle, the system including a hanging bottle casing unit for determining an overall gravity of the hanging bottle, a hanging bottle cap unit for determining a liquid density in the hanging bottle, a transmission unit for transmitting the overall gravity and liquid density of the hanging bottle to a server. The server is configured to determine a liquid gravity in the hanging bottle, calculate a liquid volume in the hanging bottle based on the liquid gravity and the liquid density, and determine a liquid level position based on the liquid volume.

Optionally, the hanging bottle casing unit includes a hanging bottle gravity detection module that uses a cantilever beam weight sensor to determine the overall gravity of the hanging bottle.

Optionally, the hanging bottle cap unit includes a liquid density detection module that uses an ultrasonic density sensor to detect the liquid density in the hanging bottle.

Optionally, the ultrasonic density sensor includes an ultrasonic transmitter and an ultrasonic receiver, both located between an outer side of a hanging bottle neck and an outer side of the hanging bottle cap, and disposed at both sides in the diametrical direction of a cross-section of the hanging bottle cap respectively, wherein the ultrasonic wave emitted from the ultrasonic transmitter passes through one end of the hanging bottle neck to reach diametrically the other end of the hanging bottle neck so as to be received by the ultrasonic receiver, such that the liquid density is calculated based on ultrasonic wave propagation parameters.

Optionally, the liquid density is calculated based on ultrasonic propagation parameters as follows:

$$\text{Liquid density } \rho = \frac{1}{kc^2} = \frac{(t-t_0)^2}{kL^2}$$

where c is the propagation velocity of the ultrasonic wave in the liquid, k is the compression coefficient, L is the cross-sectional diameter of the inner wall of the hanging bottle, t is the time the ultrasonic wave propagates between the transmitter and the receiver, and $t_0$ is the time the ultrasonic wave propagates in the walls of the hanging bottle.

Optionally, the determining the liquid gravity in the hanging bottle and calculating the liquid volume in the hanging bottle based on the liquid gravity and the liquid density includes determining the liquid gravity in the hanging bottle as $G_1-G$, and calculating the liquid volume by $V=(G_1-G)/g\rho$, where g is the gravitational acceleration, $\rho$ is the liquid density, $G_1$ is the overall gravity of the hanging bottle, and G is the gravity of the empty bottle.

Optionally, the hanging bottle cap unit includes a liquid gravity detection module that uses a micro weight sensor to detect a liquid gravity $G_2$ in the hanging bottle.

Optionally, the determining the liquid gravity in the hanging bottle and calculating the liquid volume in the hanging bottle based on the liquid gravity and the liquid density further includes, when the liquid volume calculated by $V=(G_1-G)/g\rho$ is smaller than a preset volume value and the liquid level position of the liquid is determined to be lower than the bottle neck position of the hanging bottle, determining the liquid gravity in the hanging bottle as $G_2$, and calculating the liquid volume by $V=G_2\ g\rho$, where g is the gravitational acceleration, $\rho$ is the liquid density, and $G_2$ is the liquid gravity measured by the liquid gravity detection module.

Optionally, the hanging bottle cap unit includes a liquid level inclination detection module that uses a tri-axial acceleration sensor to detect a liquid level inclination in the hanging bottle with respect to the horizontal plane.

Optionally, the liquid level position of the liquid is determined from the liquid volume and the capacity of the hanging bottle.

Optionally, a liquid flow rate is determined based on the amount of liquid volume change in the hanging bottle in a period of time.

Optionally, a liquid level inclination, a liquid level position, a liquid volume, a liquid gravity, and/or a liquid flow rate are transmitted to a terminal device, which displays in real time the liquid level inclination, the liquid level position, the liquid volume, the liquid gravity, and/or the liquid flow rate, and outputs warning information based on comparison results of the liquid volume, the liquid flow rate and/or the liquid level inclination with respective threshold values.

According to an aspect of the present disclosure, there is provided a liquid detecting method for detecting a liquid level position of a liquid in a hanging bottle, the method includes determining an overall gravity of the hanging bottle, determining a liquid density in the hanging bottle, transmitting the overall gravity and liquid density of the hanging bottle to a server, determining a liquid gravity in the hanging bottle, calculating a liquid volume in the hanging bottle from the liquid gravity and the liquid density, and determining a liquid level position based on the liquid volume by using a server.

Optionally, the overall gravity of the hanging bottle is determined using a cantilever beam weight sensor.

Optionally, the liquid density in the hanging bottle is detected using an ultrasonic density sensor.

Optionally, the ultrasonic density sensor includes an ultrasonic transmitter and an ultrasonic receiver, both located between an outer side of a hanging bottle neck and an outer side the hanging bottle cap, and disposed at both sides in the diametrical direction of a cross-section of the hanging bottle cap respectively. The ultrasonic wave emitted from the ultrasonic transmitter passes through one end of the hanging bottle neck to reach diametrically the other end of the hanging bottle neck so as to be received by the ultrasonic receiver, such that the liquid density is calculated based on ultrasonic wave propagation parameters.

Optionally, the liquid density is calculated based on ultrasonic propagation parameters as follows:

$$\text{Liquid density } \rho = \frac{1}{kc^2} = \frac{(t-t_0)^2}{kL^2}$$

where c is the propagation velocity of the ultrasonic wave in the liquid, k is the compression coefficient, L is the cross-sectional diameter of the inner wall of the hanging bottle, t is the time the ultrasonic wave propagates between the transmitter and the receiver, and $t_0$ is the time the ultrasonic wave propagates in the walls of the hanging bottle.

Optionally, the determining the liquid gravity in the hanging bottle and calculating the liquid volume in the hanging bottle based on the liquid gravity and the liquid density includes determining the liquid gravity in the hanging bottle as $G_1-G$, and calculating the liquid volume by $V=(G_1-G)/g\rho$, where g is the gravitational acceleration, $\rho$ is the liquid density, $G_1$ is the overall gravity of the hanging bottle, and G is the gravity of the empty bottle.

Optionally, the method further includes detecting a liquid gravity $G_2$ in the hanging bottle using a micro-weight sensor.

Optionally, the determining the liquid gravity in the hanging bottle and calculating the liquid volume in the hanging bottle based on the liquid gravity and the liquid density further includes, when the liquid volume calculated by $V=(G_1-G)/g\rho$ is smaller than a preset volume value and the liquid level position of the liquid is determined to be lower than the bottle neck position of the hanging bottle, determining the liquid gravity in the hanging bottle as $G_2$, and calculating the liquid volume by $V=G_2\ g\rho$, where g is the gravitational acceleration, $\rho$ is the liquid density, and $G_2$ is the liquid gravity measured by the liquid gravity detection module.

Optionally, the method further includes using a triaxial acceleration sensor to detect a liquid level inclination in the hanging bottle with respect to the horizontal plane.

Optionally, the liquid level position of the liquid is determined based on the liquid volume and the capacity of the hanging bottle.

Optionally, a liquid flow rate is determined based on the amount of liquid volume change in the hanging bottle in a period of time.

Optionally, the method further includes transmitting a liquid level inclination, a liquid level position, a liquid volume, a liquid gravity and/or liquid flow rate to a terminal device, the terminal device displaying in real time the liquid level inclination, the liquid level position, the liquid volume, the liquid gravity and/or the liquid flow rate, and outputting warning information based on comparison results of the liquid volume, the liquid flow rate and/or the liquid level inclination with respective threshold values.

The technical solution of the disclosure is simple in design, and is easy to disassemble and recycle. In addition, the detecting equipment does not need much contact with the medical liquid, and real-time measurement of the medical liquid volume and other parameters by the weight and density.

BRIEF DESCRIPTION OF THE DRAWINGS

Exemplary embodiments of the present disclosure may be more fully understood by reference to the following drawings:

FIGS. 5, 5A, and 5B show a schematic diagram of exemplary measurement ranges and structural dimensions of a liquid gravity detection module 302 according to an exemplary embodiment of the present disclosure;

DETAILED DESCRIPTION

Figure 1:
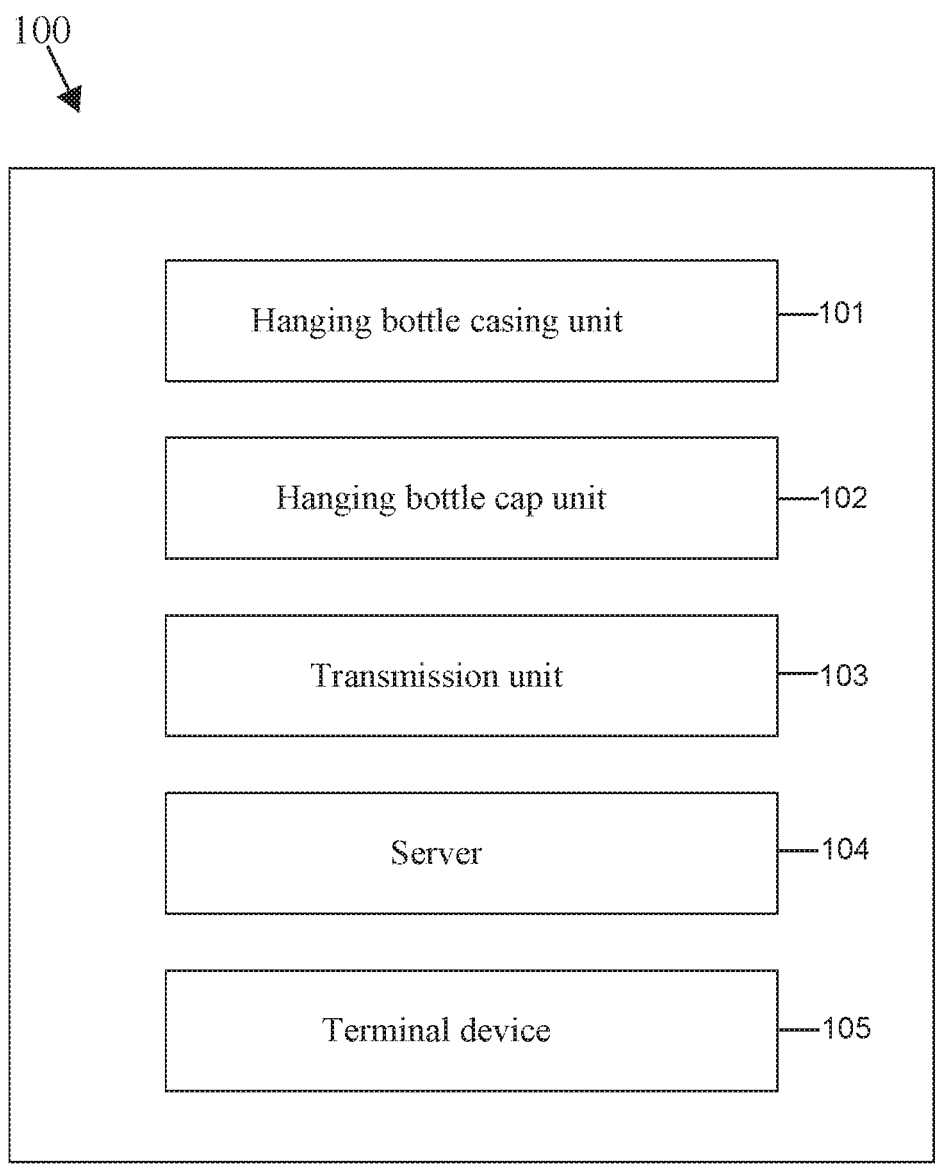
FIG. 1 shows a schematic diagram of the structure of a liquid detection system 100 according to an exemplary embodiment of the present disclosure.

Exemplary embodiments of the present disclosure will now be described with reference to the accompanying drawings, however, the disclosure may be embodied in many different forms and is not limited to the embodiments described herein, which are provided for the purpose of providing a detailed and complete disclosure of the present disclosure, and fully conveying the scope of the disclosure to those skilled in the art. The terminology shown in the exemplary embodiments in the drawings is not intended to be limiting of the present disclosure. In the drawings, the same elements/components generally use the same or similar reference numerals.

As used herein, the terms (including scientific and technical terms) have the meanings commonly understood to one skilled in the art, unless otherwise indicated. In addition, it is to be understood that a term defined in commonly used dictionaries should be understood to have a consistent meaning in the context of its associated domain, and should not be interpreted as an idealized or overly formal meaning.

FIG. 1 shows a schematic diagram of a structure of a liquid detection system 100 according to an exemplary embodiment of the present disclosure. As shown in FIG. 1, the liquid detection system 100 includes a hanging bottle casing unit 101, a hanging bottle cap unit 102, a transmission unit 103, a server 104, and a terminal device 105. As shown in FIG. 1, the liquid detection system 100 detects the liquid parameters by a non-contact intelligent integration method. Optionally, the liquid detection system 100 integrates the detection components for liquid-related parameters (e.g., level position) of a medical hanging bottle into a hanging bottle casing unit and a hanging bottle cap unit, detects in real time the liquid-related parameters by the hanging bottle casing unit and the hanging bottle cap unit, and transmits (by wired or wireless means) the liquid-related parameters in real time to the server. The server analyzes and calculates the liquid-related parameters to obtain parameters such as liquid level inclination, liquid level position, liquid volume, liquid gravity and/or liquid flow rate. The server sends parameters, such as liquid level inclination, liquid level position, liquid volume, liquid gravity and/or liquid flow rate, to the terminal device so that the user can observe the liquid level and other parameters through the terminal device. Optionally, the liquid detection system 100 may also set an alarm threshold such that when the parameters such as liquid level inclination, liquid level position, liquid volume, liquid gravity and/or liquid flow rate exceed the alarm threshold, an alarm is made by the terminal device. In addition, since all the detection circuits are integrated in the hanging bottle casing unit and the hanging bottle cap unit, only combining the hanging bottle casing unit and the hanging bottle cap unit is required to obtain the liquid-related parameters in the hanging bottle, and accordingly, no modification to the hanging bottle is needed, and the hanging bottle system can be easily commissioned and reused.

Optionally, the hanging bottle casing unit 101 is used to determine the overall gravity (i.e., weight) of the hanging bottle. The overall gravity of the hanging bottle is the sum of gravity of the empty bottle and the liquid (for example, a medical liquid) in the hanging bottle. The overall gravity of the hanging bottle is an important parameter for determining the liquid gravity in the hanging bottle. In addition, the liquid detection system 100 predetermines and stores the specifications and gravity of the hanging bottle. Optionally, the specifications and gravity of the hanging bottle can be stored in the server 104 in advance.

Optionally, the hanging bottle cap unit 102 is used to determine the liquid density in the hanging bottle, the liquid gravity and the liquid level inclination. In general, when a hanging bottle is used for drip infusion, other medical liquids are usually injected into the original liquid in the hanging bottle. The mixing of the liquids may cause a change in the liquid density in the hanging bottle, and the liquid density in the hanging bottle varies according to the types and amounts of the liquids injected. The hanging bottle cap unit 102 is capable of detecting in real time the liquid density in the hanging bottle as an important parameter for calculating the liquid volume. Optionally, the hanging bottle cap unit 102 is also capable of determining the liquid gravity and the liquid level inclination. The liquid gravity refers to the liquid gravity in the hanging bottle, and the liquid level inclination is the angle formed by the liquid level in the hanging bottle and the horizontal plane.

Optionally, the transmission unit 103 is used to transmit parameters such as liquid level inclination, the overall gravity of the hanging bottle, the liquid gravity, and the like, to the server. The transmission unit 103 may transmit parameters such as liquid level inclination, the overall gravity of the hanging bottle, the liquid gravity, and the like, to the server using any wireless or wired means. It will be appreciated that in the present embodiment, while a single transmission unit 103 is shown as an example, a transmission unit for transmitting related parameters may be located in the hanging bottle unit 101 and the hanging bottle cap unit 102, respectively.

Optionally, the server 104 is used to determine the liquid gravity in the hanging bottle and to calculate the liquid volume in the hanging bottle based on the liquid gravity and the liquid density and to determine the liquid level position based on the liquid volume. Herein, the liquid volume is calculated from the overall gravity of the hanging bottle, the gravity of the hanging bottle and the liquid density when the liquid level is above the hanging bottle neck position, and the liquid volume is calculated from the liquid gravity and the liquid density when the liquid level is below the hanging bottle neck position. Optionally, the basis for determining whether the liquid level is above the hanging bottle neck position may be that the liquid level is determined to be above the hanging bottle neck position when the liquid volume calculated from the overall gravity of the hanging bottle, the gravity of the hanging bottle, and the liquid density is greater than or equal to a preset volume value, and the liquid level is determined to be below the hanging bottleneck position when the liquid volume calculated from the overall gravity of the hanging bottle, the gravity of the hanging bottle and the liquid density is less than the preset volume value. Optionally, the user may set the preset volume value to any reasonable value, such as a liquid volume corresponding to the liquid level at the hanging bottle neck position or to the liquid level above the hanging bottle neck position by 1 cm, depending on the actual needs. Typically, the hanging bottle is used topside down, and the hanging bottle neck position and the hanging bottle capacity is fixed. Optionally, the server 104 determines the liquid level position based on the liquid volume, typically based on the liquid volume and the parameters of the hanging bottle, such as capacity, size, and the like of the hanging bottle. For example, a specific liquid volume corresponds to a liquid level position of the liquid one-to-one, without considering the liquid level inclination. In the case of considering the liquid level inclination, the liquid level position of the liquid will be modified according to the liquid level inclination.

Optionally, the server 104 also includes an interface unit (not shown) for receiving parameters such as overall gravity of the hanging bottle, liquid gravity, liquid level inclination, and liquid density, as well as for sending parameters such as liquid volume, liquid level, liquid flow rate and liquid level inclination. The server 104 also includes a storage unit (not shown) for storing various related data, such as specifications, dimensions, gravities, and the like, of various hanging bottles.

Optionally, the terminal device 105 is used to receive parameters such as liquid level inclination, liquid level position, liquid volume, liquid gravity, infusion time, and/or liquid flow rate. The liquid level, liquid volume, liquid gravity, infusion time and/or liquid flow rate are displayed in real time on the terminal device 105, and the terminal device compares the liquid volume, liquid flow rate and/or liquid level inclination with the respective threshold values, and output warning information based on a comparison result. Optionally, the user may input parameters such as specifications of the hanging bottle through the terminal device 105 before using the hanging bottle, and the terminal device 105 may send the parameters to the server 104. On the other hand, the hanging bottle cap unit 102 can be used to detect parameters such as specifications of the hanging bottle, and send them to the server 104 through the transmission unit. The terminal device 105 may bi-directionally communicate with the server 104, and the server 104 may output the calculated liquid parameters (by wired or wireless means) to the terminal device 105. The terminal device 105 may be a portable device such as mobile phone, PAD, etc., to facilitate the use by a caregiver; or it may be a mainframe to facilitate the control room personnel to simultaneously monitor the states of a plurality of infusion hanging bottles.

Figure 2:
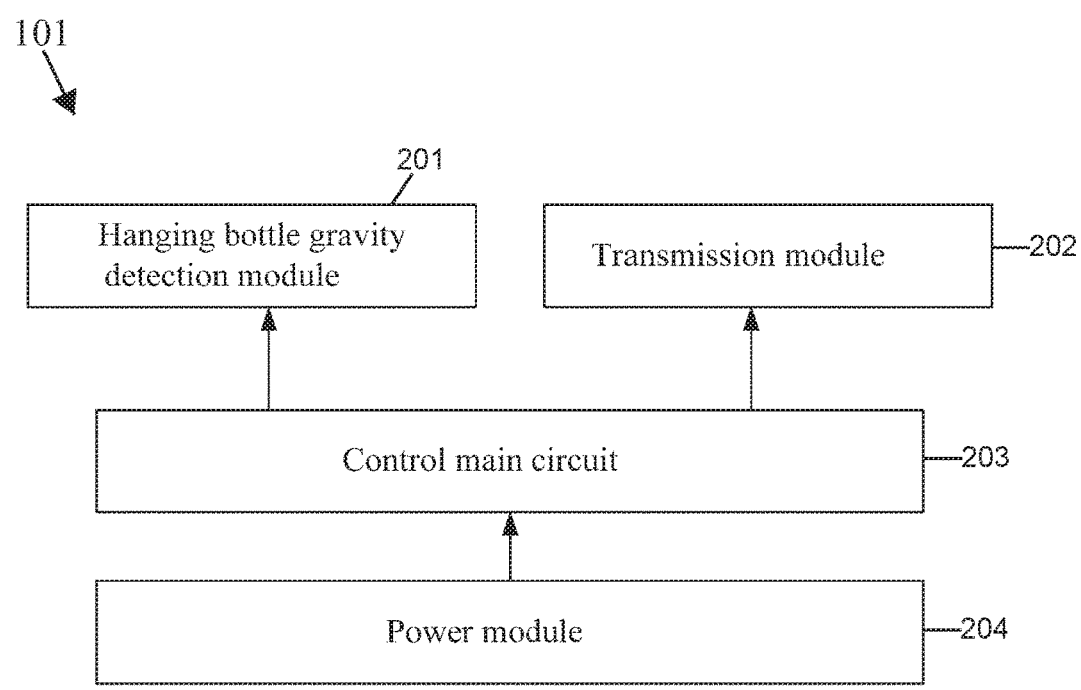
FIG. 2 shows a schematic diagram of a structure of a hanging bottle casing unit 101 according to an exemplary embodiment of the present disclosure.

FIG. 2 shows a schematic diagram of a structure of a hanging bottle casing unit 101 according to an exemplary embodiment of the present disclosure. As shown in FIG. 2, the hanging bottle casing unit 101 includes a hanging bottle gravity detection module 201, a transmission module 202, a control main circuit 203, and a power supply module 204. Optionally, the hanging bottle gravity detection module 201 uses a cantilever beam weight sensor to detect the overall gravity of the hanging bottle in real time. The overall gravity of the hanging bottle consists of the gravity of the empty bottle and the liquid gravity in the hanging bottle. Optionally, the transmission module 202 transmits the overall gravity of the hanging bottle to the server by wired or wireless means. Alternatively, the hanging bottle casing unit 101 transmits the overall gravity of the hanging bottle to the server through an external transmission module. Optionally, the control main circuit 203 is used for controlling the various devices inside the hanging bottle casing unit 101, for example, controlling the power module 204 to supply power to the hanging bottle gravity detection module 201 or the transmission module 202, and controlling the hanging bottle gravity detection module 201 to perform gravity measurement and controlling the transmission module for data transmission. Optionally, the power supply module 204 is used to power the hanging bottle casing unit 101.

Figure 3:
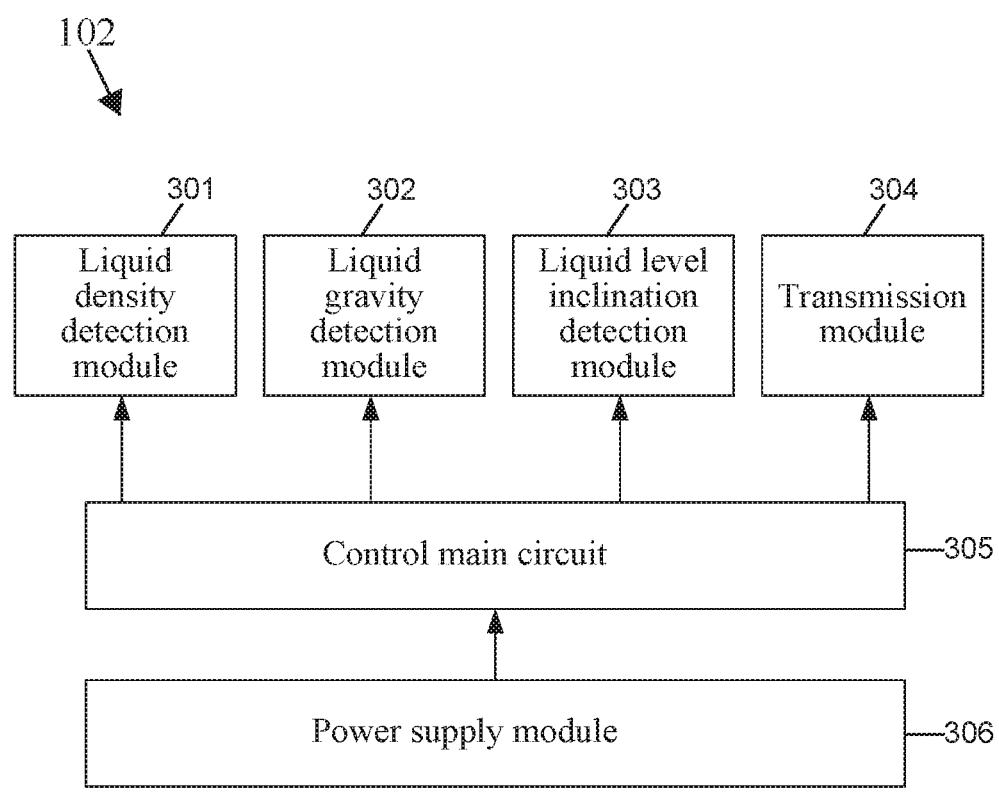
FIG. 3 shows a schematic diagram of a structure of a hanging bottle cap unit 102 according to an exemplary embodiment of the present disclosure.

FIG. 3 shows a schematic diagram of a structure of a hanging bottle cap unit 102 according to an exemplary embodiment of the present disclosure. As shown in FIG. 3, the hanging bottle cap unit 102 includes a liquid density detection module 301, a liquid gravity detection module 302, a liquid level inclination detection module 303, a transmission module 304, a control main circuit 305, and a power supply module 306.

Figure 4:
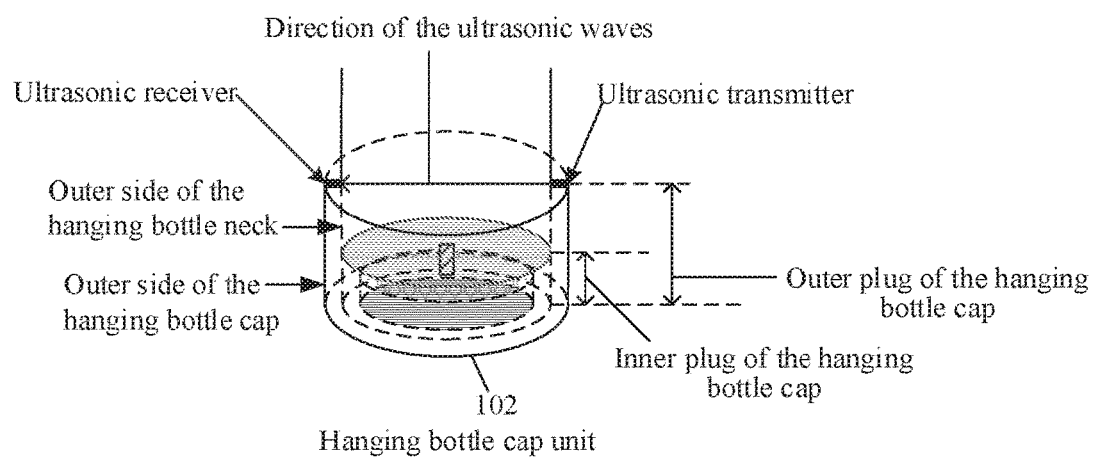
FIG. 4 shows a schematic diagram of a detailed structure of a hanging bottle cap unit 101 according to an exemplary embodiment of the present disclosure.

Optionally, the liquid density detection module 301 uses an ultrasonic density sensor to detect the liquid density in the hanging bottle. FIG. 4 shows a schematic diagram of a detailed structure of a hanging bottle cap unit 102 according to an exemplary embodiment of the present disclosure. As shown in FIG. 4, the ultrasonic density sensor includes an ultrasonic transmitter and an ultrasonic receiver. The ultrasonic transmitter and the ultrasonic receiver are located between the outer side of the hanging bottle neck and the outer side of the hanging bottle cap, and are arranged at both ends in the diametrical direction of the cross section of the hanging bottle cap. The ultrasonic wave emitted from the ultrasonic emitter passes through one end of the hanging bottle neck to reach diametrically the other end of the hanging bottle neck so as to be received by the ultrasonic receiver, so that the liquid density is calculated on the basis of the ultrasonic wave propagation parameters. As the penetration of an ultrasonic wave is strong, the ultrasonic transmitter and ultrasonic receiver only need to be disposed on the outer side of the hanging bottle so as to avoid contamination of the liquid.

The ultrasonic transmitter and receiver are adhered tightly to the outer side of the hanging bottle neck, forming an outer plug of the hanging bottle cap. The ultrasonic transmitter emits ultrasonic waves through the wall of the hanging bottle, through the liquid, and then through the wall on the other side of the hanging bottle to reach the ultrasonic receiver. The ultrasonic transmitter and the ultrasonic receiver may be composed of an ultrasonic transducer which generates an ultrasonic wave by a piezoelectric effect.

The propagation velocity of an ultrasonic wave in a liquid is as follows:

$$c = \frac{1}{\sqrt{\rho k}}$$

where c is the propagation velocity of the ultrasonic wave in the liquid, $\rho$ is the liquid density, and k is the compression coefficient. As the liquid is an aqueous solution, the compression coefficient is basically unchanged, as a constant.

The propagation velocity of the ultrasonic wave in the liquid can be measured by the ultrasonic transmission time t in a fixed propagation distance L, namely:

$$c = \frac{L}{t}$$

where L is a constant and is the diameter of the cross-section of the hanging bottle neck.

Optionally, the accuracy of t depends on the frequency of the clock circuit. At present, the clock frequency can be up to 10 MHz or more, then the minimum timing accuracy can be at least $$\frac{1}{10 \text{ MHz}} = 0.1 \ \mu s.$$

The minimum diameter of the hanging bottle neck is 0.02 m, the propagation velocity of the ultrasonic wave in the liquid is less than 2000 m/s, then the minimum propagation time of the ultrasound wave in the hanging bottle neck is $$\frac{0.02 \text{ m}}{2000 \text{ m/s}} = 10 \ \mu s \gg 0.1 \ \mu s,$$

so it is feasible to record the propagation time of the ultrasonic wave.

In addition, before measuring the liquid density by the liquid density detection module 301, it is also necessary to measure the propagation time of the ultrasonic wave in the wall of the hanging bottle neck. That is, it is necessary to measure in advance the propagation time of the ultrasonic wave in the glass body of the hanging bottle wall at the hanging bottle neck. Typically, the propagation time $t_1$ of the ultrasonic wave through the walls of the hanging bottle and the air can be recorded by keeping the hanging bottle upside up. As the propagation velocity $v_{empty}$ of the ultrasonic wave in the air is fixed, the size $L_{empty}$ of the inner periphery the hanging bottle is also determinable, the propagation time of the ultrasonic wave in the hanging bottle can be obtained by $$t_{empty} = \frac{L_{empty}}{v_{empty}},$$

where $L_{empty}$ is the diameter of the inner periphery of the cross-section of the hanging bottle neck. Therefore, we can get the propagation time of the ultrasonic wave in the walls of the hanging bottle, $t_0 = t_1 - t_{empty}$.

From the above formulas, it can be concluded that the liquid density is:

$$\rho = \frac{1}{kc^2} = \frac{(t-t_0)^2}{kL^2}.$$

Optionally, according to an exemplary embodiment of the present disclosure, the propagation times of the ultrasonic wave in the walls of the hanging bottles of various types or sizes may be stored in a storage unit (not shown) of the hanging bottle cap unit or a storage unit of the server. When the liquid density is calculated by the above formula, the propagation time of the ultrasonic wave in the walls of the hanging bottle is read from the storage unit of the hanging bottle cap unit, or from the server.

Optionally, the liquid gravity detection module 302 uses a micro-weight sensor contained therein (not shown in FIGS. 5, 5A and 5B) to detect the gravity $G_2$ of the liquid in the hanging bottle. FIGS. 5, 5A, and 5B illustrate a schematic diagram of exemplary measurement ranges and structural dimensions of a liquid gravity detection module 302 according to an exemplary embodiment of the present disclosure. FIG. 5A is a bottom-up view of the liquid gravity detection module 302, and FIG. 5B is a side view of the liquid gravity detection module 302. As shown in FIG. 5A, 3-M indicates screw holes whose centers are positioned along a circle having a diameter of φD. The inner circle in FIG. 5A indicates a cover plate of the liquid gravity detection module 302. As shown in FIG. 5B, the liquid gravity detection module 302 includes a housing 501, a lead 502 and a probe 503. The probe 503 is configured to detect a gravity of the liquid. In a table of FIG. 5, φA indicates a diameter of the housing 501, φC indicates a diameter of the probe 503, φD indicates a diameter of the circle along which screw holes 3-M are positioned, φH indicates a height of the housing 501 and the probe 503, and φH indicates a height of the housing 501. The liquid gravity detection module 302 can be placed inside the hanging bottle cap unit to accurately monitor the pressure exerted by the liquid in the hanging bottle neck against the hanging bottle cap, i.e., the gravity. The maximum size of the gravity sensor is only 2 cm, and it can be placed inside the hanging bottle cap.

Optionally, the liquid level inclination detection module 303 detects the liquid level inclination α using a triaxial acceleration sensor. Optionally, the liquid level inclination is the angle formed by the liquid level of the liquid in the hanging bottle and the horizontal plane. Typically, the liquid level inclination can reflect the tilt angle of the hanging bottle. When the liquid level inclination is greater than a predetermined threshold value, it can be shown that the tilt angle of the hanging bottle is in a dangerous state.

Optionally, the transmission module 304 communicates parameters such as liquid density, liquid gravity, and liquid level inclination to the server by wired or wireless means. Alternatively, the hanging bottle cap unit 102 transmits parameters such as liquid density, liquid gravity, and liquid level inclination to the server through an external transmission module. Optionally, the transmission module 304 may receive the liquid density, liquid gravity, and liquid level inclination parameters from the control main circuit 305.

Optionally, the control main circuit 305 is used to control the various devices inside the hanging bottle cap unit 102, for example, controlling the power supply module 306 to power the liquid density detection module 301, liquid gravity detection module 302, liquid level inclination detection module 303, and transmission module 304, controlling the liquid density detection module 301 to determine the liquid density in the hanging bottle, controlling the liquid gravity detection module 302 to determine the liquid gravity in the hanging bottle, and controlling the liquid level inclination detection module 303 to determine the liquid level inclination in the hanging bottle. The control main circuit 305 may also obtain the liquid density in the hanging bottle from the liquid density detection module 301, obtain the liquid gravity in the hanging bottle from the liquid gravity detection module 302 and obtain the liquid level inclination in the hanging bottle from the liquid level inclination detection module 303. Then the control main circuit may transmit the related data through the wireless transmission module to the server. The main control circuit may only transmit the data to the server, without performing much processing on the data. Optionally, the power supply module 306 is used to power the hanging bottle cap unit 102.

Optionally, the server 104 obtains parameters such as the overall gravity of the hanging bottle, liquid density, liquid gravity, liquid level inclination from the hanging bottle casing unit and the hanging bottle cap unit. Optionally, the server 104 also includes a storage unit (not shown) for storing various related data, such as specifications, dimensions, gravities and the like of the various hanging bottles. The server 104 is used to calculate the liquid volume in the hanging bottle according to the overall gravity of the hanging bottle, the liquid density, the liquid gravity, the gravity of the hanging bottle, and the like.

Specifically, the server 104 processes the data transmitted from the hanging bottle casing unit and the hanging bottle cap unit. The data received from the hanging bottle casing unit and the hanging bottle cap unit include the overall gravity $G_1$ of the hanging bottle, the liquid gravity $G_2$, the liquid density ρ, and the liquid level inclination α. In addition, the server 104 may obtain the gravity G of the empty bottle from a database of the storage unit.

Optionally, when the liquid level is above the hanging bottle neck, the server 104 determines the liquid gravity through the overall gravity $G_1$ of the hanging bottle and the gravity G of the empty bottle. Therefore, the liquid volume is:

$$V = \frac{G_1 - G}{g\rho}.$$

where g is the gravitational acceleration, p is the liquid density, G1 is the overall gravity of the hanging bottle In addition, since the error of the liquid volume obtained by the overall gravity $G_1$ of the hanging bottle and the gravity G of the empty bottle is large when the liquid level is lower than the hanging bottle neck, the liquid gravity $G_2$ determined by the liquid gravity detection module is used to calculate the liquid volume. That is, when $G_2 \subset [G_1-G-\Delta G, G_1-G+\Delta G]$, where $\Delta G$ is a gravitational threshold, $G_2$ is used to calculate the liquid volume, that is:

$$V = \frac{G_2}{g\rho}$$

where g is the gravitational acceleration, p is the liquid density, and $G_2$ is the liquid gravity $G_2$ determined by the liquid gravity detection module.

Optionally, the server 104 can also record the corresponding infusion time T, i.e., the time value from the start of infusion to the present. The server 104 may send the time value to the terminal device to be displayed to the user by the terminal device. Optionally, the server 104 may also calculate the liquid flow rate from a change in the liquid volume per unit time, that is $$\upsilon = \frac{\Delta V}{\Delta T}$$

where $\Delta V$ is the amount of liquid volume change over a time $\Delta T$.

The server 104 may send the liquid flow rate to the terminal device to be displayed to the user by the terminal device.

Optionally, the terminal device 105 is used to receive parameters such as liquid level inclination, liquid level position, liquid volume, liquid gravity, infusion time, and/or liquid flow rate. The server 104 and the terminal device 105 may perform bi-directional transmission, and the server may obtain data from the hanging bottle casing unit 101 or the hanging bottle cap unit 102, perform corresponding measurement on the data, and then output the data to the terminal device 105. The terminal device 105 may be a wired or wireless terminal device, for example, a mobile device such as mobile phone, PAD, etc., to facilitate the use by a caregiver, or a mainframe to facilitate the control room personnel to simultaneously monitor the states of a plurality of infusion hanging bottles.

The terminal device 105 may well interact with other components of the liquid detection system 100 in real time. The terminal device 105 can display the parameters of the liquid in the hanging bottle in real time, such as liquid density, liquid volume, liquid gravity and infusion time, etc., and can also set parameters of the liquid detection system in a wireless terminal, so that a warning may be issued. The user can not only get the parameters, but also can set corresponding personalized warning thresholds, that is, a liquid volume warning value $V_0$, liquid flow rate warning value $\upsilon_0$, liquid level inclination warning value $α_0$. Different users can have different warning values. That is, when $V \leq V_0$ or $v \geq v_0$ or $v \leq v_0$ or $|α| \geq α_0$, the display terminal can issue a corresponding warning.

Figure 6:
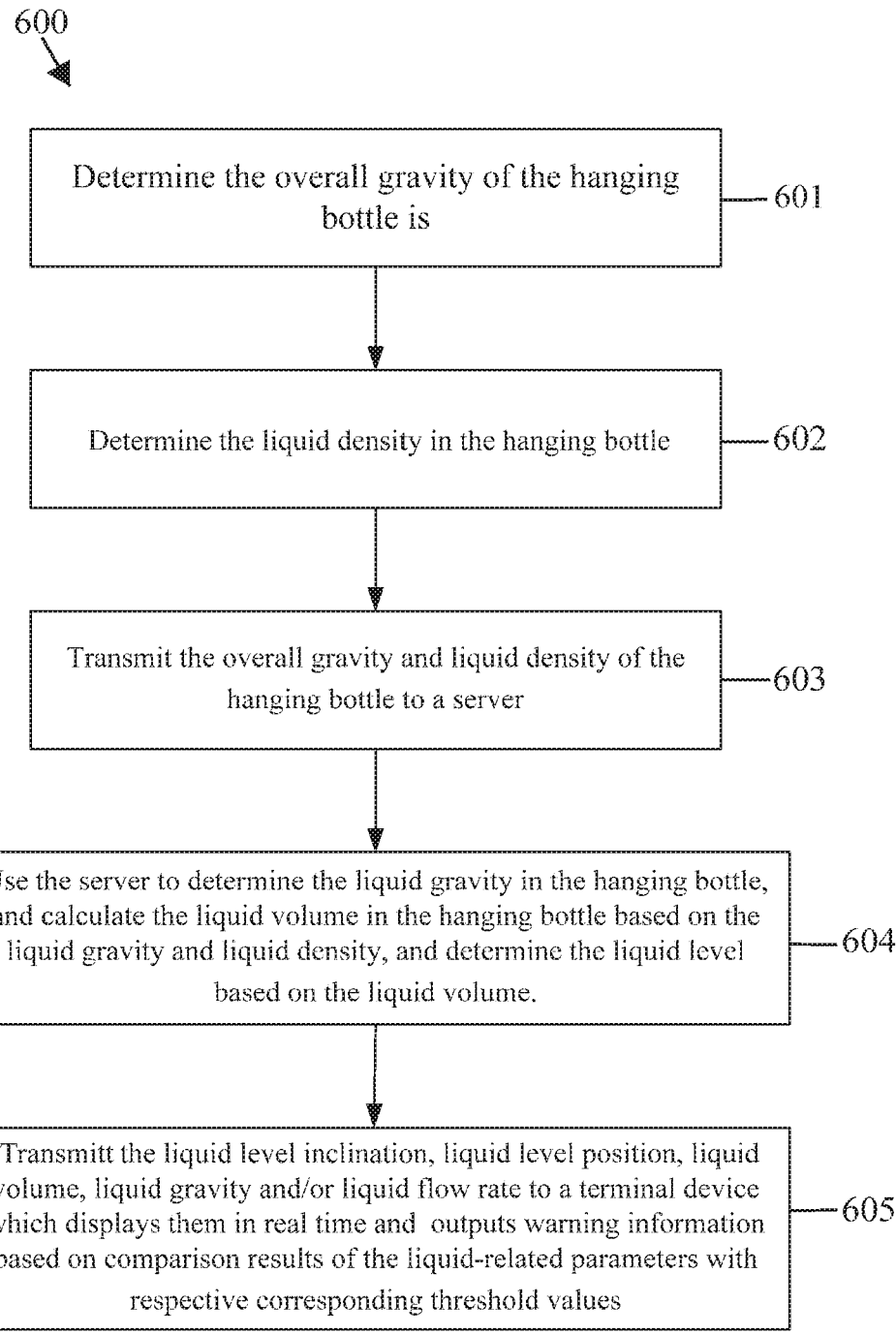
FIG. 6 shows a flow diagram of a liquid detection method 600 according to an exemplary embodiment of the present disclosure.

FIG. 6 shows a flow diagram of a liquid detection method 600 according to an exemplary embodiment of the present disclosure. As shown in FIG. 6, the liquid detection method 600 detects liquid parameters by a non-contact intelligent integration method. The liquid detection method 600 is suitable for integrating detection components for liquid-related parameters (e.g., liquid level position) of a medical hanging bottle into a system of a hanging bottle casing unit and a hanging bottle cap unit. The liquid detection method 600 detects the liquid-related parameters of the hanging bottle through the hanging bottle casing unit and the hanging bottle cap unit in real time, and transmits (by wired or wireless means) the liquid-related parameters in real time to the server. The server analyzes and calculates the liquid-related parameters to obtain parameters such as liquid level inclination, liquid level position, liquid volume, liquid gravity and/or liquid flow rate. The server sends parameters such as liquid level inclination, liquid level position, liquid volume, liquid gravity and/or liquid flow rate to the terminal device so that the user can observe the liquid level and other parameters through the terminal device.

Optionally, at step 601, the overall gravity of the hanging bottle is determined by the hanging bottle casing unit. Herein the hanging bottle casing unit uses a cantilever beam weight sensor to determine the overall gravity of the hanging bottle.

Optionally, in step 602, the liquid density in the hanging bottle is determined by the hanging bottle cap unit. Optionally, the hanging bottle cap unit uses an ultrasonic density sensor to detect the liquid density in the hanging bottle. Herein the ultrasonic density sensor comprises an ultrasonic transmitter and an ultrasonic receiver which are located between the outer side of the hanging bottle neck and the outer side of the hanging bottle cap and are arranged at both sides in the diametrical direction of the cross-section of the hanging bottle cap respectively. The ultrasonic wave emitted from the ultrasonic transmitter pass through one end of the hanging bottle neck to reach diametrically the other end of the hanging bottle neck to be received by the ultrasonic receiver, and the liquid density is calculated according to ultrasonic wave propagation parameters.

Optionally, the liquid density is calculated from the ultrasonic propagation parameters in particular as follows:

$$\text{Liquid density } \rho = \frac{1}{kc^2} = \frac{(t-t_0)^2}{kL^2},$$

where c is the propagation velocity of the ultrasonic wave in the liquid, k is the compression coefficient, L is the cross-sectional diameter of the inner wall of the hanging bottle, t is the time the ultrasonic wave propagates between the transmitter and the receiver, and $t_0$ is the time the ultrasonic wave propagates in the walls of the hanging bottle.

Optionally, the liquid level inclination is also measured by means of a liquid level inclination detection module of the hanging bottle cap unit. And the liquid level inclination detection module detects the inclination angle of the liquid level in the hanging bottle and the horizontal plane by using a triaxial acceleration sensor.

Optionally, at step 603, a transmission unit is used to transmit the overall gravity and liquid density of the hanging bottle to a server. The transmission unit may transmit the overall gravity and liquid density of the hanging bottle to the server by wired/wireless means.

Optionally, at step 604, the server is used to determine the liquid gravity in the hanging bottle, and calculate the liquid volume in the hanging bottle based on the liquid gravity and liquid density, and determine the liquid level based on the liquid volume. Herein, determining the liquid gravity in the hanging bottle and calculating the liquid volume in the hanging bottle based on the liquid gravity and the liquid density includes determining the liquid gravity in the hanging bottle as $G_1-G$, and calculating the liquid volume by $V=(G_1-G)/g\rho$. Herein, g is the gravitational acceleration, $\rho$ is the liquid density, $G_1$ is the overall gravity of the hanging bottle, and G is the gravity of the empty bottle.

Optionally, the hanging bottle cap unit further includes a liquid gravity detection module that uses a micro-load sensor to detect the gravity $G_2$ of the liquid in the hanging bottle. And the determining the liquid gravity in the hanging bottle and calculating the liquid volume in the hanging bottle based on the liquid gravity and the liquid density further comprises: when the liquid volume calculated by $V=(G_1-G)/g\rho$ is less than a preset volume value and the liquid level position is determined to be lower than the bottle neck position of the hanging bottle, determining the liquid gravity in the hanging bottle as $G_2$, and calculating the liquid volume in the hanging bottle by $V=G_2/g\rho$. Herein, g is the gravitational acceleration, $\rho$ is the liquid density, and $G_2$ is the liquid gravity measured by the liquid gravity detection module. Optionally, the liquid level position of the liquid is determined from the liquid volume and the capacity of the hanging bottle.

Optionally, when the liquid can be determined in real time, a liquid flow rate is determined based on the amount of liquid volume change in the hanging bottle during a period of time.

Optionally, at step 605, the liquid level inclination, liquid level position, liquid volume, liquid gravity and/or liquid flow rate are transmitted to a terminal device which displays in real time the liquid level inclination, liquid level position, liquid volume, liquid gravity, and/or liquid flow rate, and outputs warning information based on comparison results of the liquid volume, liquid flow rate and/or liquid level inclination with respective corresponding threshold values.

Figure 7:
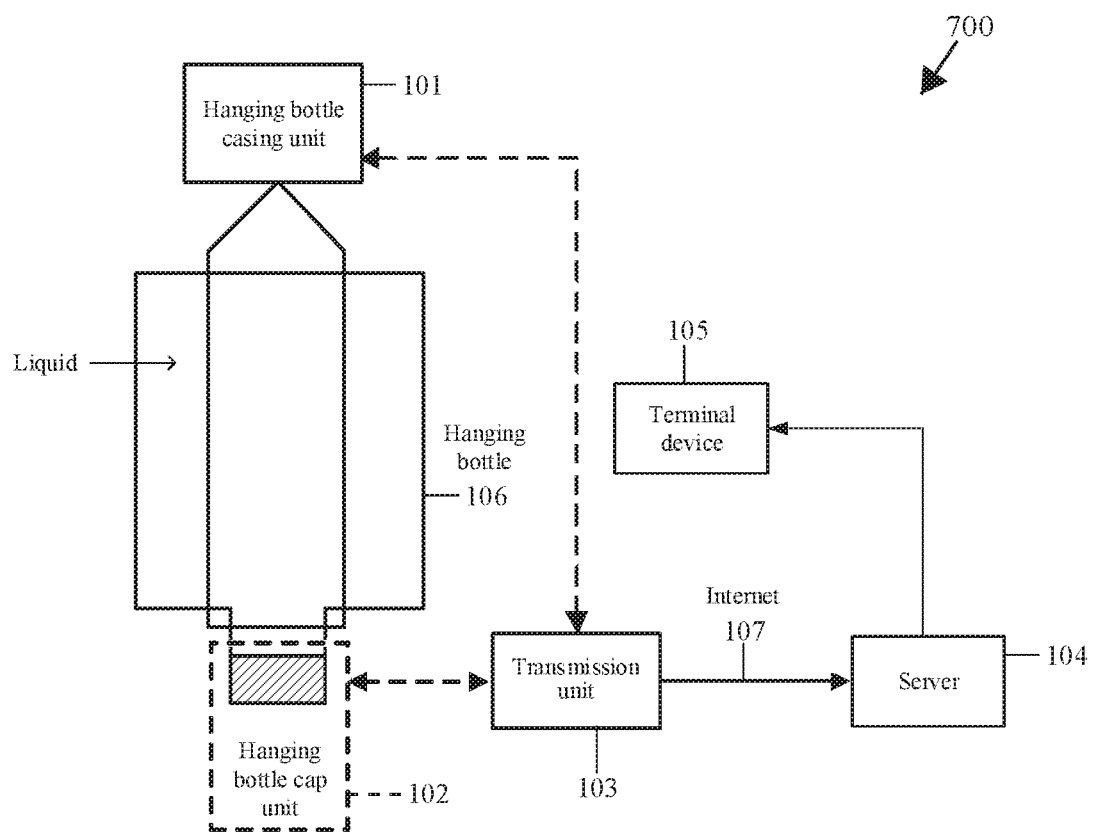
FIG. 7 shows a schematic diagram of a structure of a liquid detection system 700 according to another exemplary embodiment of the present disclosure.

FIG. 7 illustrates a schematic diagram of a structure of a liquid detection system 700 according to another exemplary embodiment of the present disclosure. As shown in FIG. 7, the liquid detection system 700 includes a hanging bottle casing unit 101, a hanging bottle cap unit 102, a hanging bottle 106, a transmission unit 103, the Internet 107, a server 104, and a terminal device 105. The liquid detection system 700 detects liquid parameters by a non-contact intelligent integration method. Optionally, the liquid detection system 700 integrates detection components for liquid-related parameters (e.g., liquid level position) of a medical hanging bottle into a hanging bottle casing unit and a hanging bottle cap unit, detects in real time by the hanging bottle casing unit and the hanging bottle cap unit the liquid-related parameters of the hanging bottle, and transmits in real time (by wired or wireless means) the liquid-related parameters to the server. The server analyzes and calculates the liquid-related parameters to obtain parameters such as liquid level inclination, liquid level position, liquid volume, liquid gravity and/or liquid flow rate. The server sends parameters such as liquid level inclination, liquid level position, liquid volume, liquid gravity and/or liquid flow rate to the terminal device so that the user can observe the liquid level and other parameters through the terminal device. Optionally, the liquid detection system 700 may also set an alarm threshold such that when the parameters such as liquid level inclination, liquid level position, liquid volume, liquid gravity and/or liquid flow rate exceed an alarm threshold, an alarm is made through the terminal device. In addition, since all the detection circuits are integrated in the hanging bottle casing unit and the hanging bottle cap unit, only combining the hanging bottle casing unit and the hanging bottle cap unit is required to obtain the liquid-related parameters in the hanging bottle, and accordingly, no modification to the hanging bottle is needed, the hanging bottle system can be easily commissioned and reused.

The disclosure has been described by reference to a few embodiments. However, it is well known to those skilled in the art that as defined in the appended patent claims, other embodiments than the above disclosed embodiments of the disclosure are equally within the scope of the disclosure.

In general, all terms used in the claims are to be interpreted according to their ordinary meaning in the technical field, unless otherwise explicitly defined therein. All references to "a/the/said device, component, etc." are to be interpreted openly as at least one instance of the stated device, component, etc., unless explicitly stated otherwise. The steps of any method disclosed herein are not necessarily required to be performed in the precise order as disclosed, unless expressly stated otherwise.

What is claimed is:

1. A liquid detection system for detecting a liquid level position of a liquid in a hanging bottle, the system comprising:
a hanging bottle casing unit configured to determine an overall gravity of the hanging bottle;
a hanging bottle cap unit configured to determine a liquid density in the hanging bottle;

a transmission unit configured to transmit the overall gravity and the liquid density of the hanging bottle to a server; and the server, wherein the server is configured to determine a liquid gravity in the hanging bottle, calculate a liquid volume in the hanging bottle based on the liquid gravity and the liquid density, and determine a liquid level position based on the liquid volume, wherein the hanging bottle casing unit comprises a hanging bottle gravity detection module configured to use a cantilever beam weight sensor to determine the overall gravity of the hanging bottle, and wherein the hanging bottle cap unit comprises a liquid density detection module configured to use an ultrasonic density sensor to detect the liquid density in the hanging bottle.

2. The apparatus according to claim 1, wherein the ultrasonic density sensor comprises an ultrasonic transmitter and an ultrasonic receiver, both located between an outer side of a hanging bottle neck and an outer side of a hanging bottle cap, and disposed at both sides in a diametrical direction of a cross-section of the hanging bottle cap respectively, wherein an ultrasonic wave emitted from the ultrasonic transmitter passes through one end of the hanging bottle neck to reach diametrically another end of the hanging bottle neck so as to be received by the ultrasonic receiver, such that the liquid density is calculated based on ultrasonic wave propagation parameters.

3. The apparatus according to claim 2, wherein the liquid density is calculated based on ultrasonic propagation parameters as follows:

$$\text{Liquid density } \rho = \frac{1}{kc^2} = \frac{(t-t_0)^2}{kL^2}$$

wherein c is a propagation velocity of the ultrasonic wave in the liquid, k is a compression coefficient, L is a cross-sectional diameter of an inner wall of the hanging bottle, t is a time the ultrasonic wave propagates between the transmitter and the receiver, and $t_0$ is a time the ultrasonic wave propagates in walls of the hanging bottle.

4. The apparatus according to claim 1, wherein determining the liquid gravity in the hanging bottle and calculating the liquid volume in the hanging bottle based on the liquid gravity and the liquid density comprises:

determining the liquid gravity in the hanging bottle as $G_1-G$, and calculating the liquid volume by $V=(G_1-G)/g\rho$, wherein g is a gravitational acceleration, $\rho$ is the liquid density, $G_1$ is the overall gravity of the hanging bottle, and G is a gravity of an empty bottle.

5. The apparatus according to claim 4, wherein the hanging bottle cap unit comprises a liquid gravity detection module configured to use a micro weight sensor to detect a liquid gravity $G_2$ in the hanging bottle.

6. The apparatus according to claim 5, wherein determining the liquid gravity in the hanging bottle and calculating the liquid volume in the hanging bottle based on the liquid gravity and the liquid density further comprises:

when the liquid volume calculated by $V=(G_1-G)/g\rho$ is smaller than a preset volume value and the liquid level position of the liquid is determined to be lower than a bottle neck position of the hanging bottle, the liquid gravity in the hanging bottle is determined as $G_2$, and the liquid volume is calculated by $V=G_2/g\rho$, wherein g is the gravitational acceleration, $\rho$ is the liquid density, and $G_2$ is the liquid gravity measured by the liquid gravity detection module.

7. The apparatus according to claim 1, wherein the hanging bottle cap unit comprises a liquid level inclination detection module configured to use a triaxial acceleration sensor to detect a liquid level inclination in the hanging bottle with respect to a horizontal plane.

8. The apparatus according to claim 1, wherein the liquid level position of the liquid is determined from the liquid volume and a capacity of the hanging bottle.

9. The apparatus according to claim 1, wherein a liquid flow rate is determined based on an amount of liquid volume change in the hanging bottle over a period of time.

10. The apparatus according to claim 1, wherein at least one of a liquid level inclination, a liquid level position, a liquid volume, a liquid gravity, a liquid flow rate are transmitted to a terminal device, and wherein the terminal device displays in real time the at least one of the liquid level inclination, the liquid level position, the liquid volume, the liquid gravity, and the liquid flow rate, and outputs warning information based on comparison results of the at least one of the liquid volume, the liquid flow rate and the liquid level inclination with respective threshold values.

11. A liquid detecting method for detecting a liquid level position of a liquid in a hanging bottle, the method comprising:

determining an overall gravity of the hanging bottle;
determining a liquid density in the hanging bottle;
transmitting the overall gravity and the liquid density of the hanging bottle to a server;
determining a liquid gravity in the hanging bottle;
calculating a liquid volume in the hanging bottle from the liquid gravity and the liquid density; and
determining the liquid level position based on the liquid volume using the server, wherein the overall gravity of the hanging bottle is determined using a cantilever beam weight sensor, and
wherein the liquid density in the hanging bottle is detected using an ultrasonic density sensor.

12. The method according to claim 11, wherein the ultrasonic density sensor comprises an ultrasonic transmitter and an ultrasonic receiver, both located between an outer side of a hanging bottle neck and an outer side of a hanging bottle cap, and disposed at both sides in a diametrical direction of a cross-section of the hanging bottle cap respectively, wherein an ultrasonic wave emitted from the ultrasonic transmitter passes through one end of the hanging bottle neck to reach diametrically another end of the hanging bottle neck so as to be received by the ultrasonic receiver, such that the liquid density is calculated based on ultrasonic wave propagation parameters.

13. The method according to claim 12, wherein the liquid density is calculated based on ultrasonic propagation parameters as follows:

$$\text{Liquid density } \rho = \frac{1}{kc^2} = \frac{(t-t_0)^2}{kL^2}$$

wherein c is a propagation velocity of the ultrasonic wave in the liquid, k is a compression coefficient, L is a cross-sectional diameter of an inner wall of the hanging bottle, t is a time the ultrasonic wave propagates between the transmitter and the receiver, and $t_0$ is a time the ultrasonic wave propagates in walls of the hanging bottle.

14. The method according to claim 13, wherein determining the liquid gravity in the hanging bottle and calculating the liquid volume in the hanging bottle based on the liquid gravity and the liquid density comprises:

determining the liquid gravity in the hanging bottle as $G_1-G$, and calculating the liquid volume by $V=(G_1-G)/g\rho$, wherein g is a gravitational acceleration, $\rho$ is the liquid density, $G_1$ is the overall gravity of the hanging bottle, and G is a gravity of an empty bottle.

15. The method according to claim 14, further comprising detecting a liquid gravity $G_2$ in the hanging bottle using a micro-weight sensor, wherein determining the liquid gravity in the hanging bottle and calculating the liquid volume in the hanging bottle based on the liquid gravity and the liquid density further comprises:

when the liquid volume calculated by $V=(G_1-G)/g\rho$ is smaller than a preset volume value and the liquid level position of the liquid is determined to be lower than a bottle neck position of the hanging bottle, determining the liquid gravity in the hanging bottle as $G_2$, and calculating the liquid volume by $V=G_2/g\rho$, wherein g is the gravitational acceleration, $\rho$ is the liquid density, and $G_2$ is the liquid gravity measured by a liquid gravity detection module.

16. The method according to claim 11, wherein the liquid level position of the liquid is determined based on the liquid volume and a capacity of the hanging bottle.

17. The method according to claim 11, wherein a liquid flow rate is determined based on an amount of liquid volume change in the hanging bottle in a period of time.

18. The method according to claim 11, further comprising:

transmitting at least one of a liquid level inclination, the liquid level position, the liquid volume, the liquid gravity, and a liquid flow rate to a terminal device, wherein the terminal device displays, in real time the at least one of the liquid level inclination, the liquid level position, the liquid volume, the liquid gravity, and the liquid flow rate; and outputting warning information based on comparison results of the at least one of the liquid volume, the liquid flow rate, and the liquid level inclination with respective threshold values.

* * * * *

UNITED STATES PATENT AND TRADEMARK OFFICE
CERTIFICATE OF CORRECTION

PATENT NO. : 10,307,537 B2
APPLICATION NO. : 15/503800
DATED : June 4, 2019
INVENTOR(S) : Chuang Wei Page 1 of 1

It is certified that error appears in the above-identified patent and that said Letters Patent is hereby corrected as shown below:

In Specification

Column 3, Line 23, delete "$V = G_2 g\rho$," and insert therefor -- $V = G_2 / g\rho$, --.
Column 4, Line 39, delete "$V = G_2 g\rho$," and insert therefor -- $V = G_2 / g\rho$, --.
Column 11, Line 37, delete "p is the liquid" and insert therefor -- $\rho$ is the liquid --.
Column 11, Line 52, delete "p is the liquid" and insert therefor -- $\rho$ is the liquid --.

Signed and Sealed this
Twenty-seventh Day of August, 2019

Andrei Iancu
*Director of the United States Patent and Trademark Office*